United States Patent
Fukushima et al.

(10) Patent No.: US 7,186,845 B2
(45) Date of Patent: Mar. 6, 2007

(54) POLYMER-FILLER COUPLING ADDITIVES

(75) Inventors: Yasuo Fukushima, Cuyahoga Falls, OH (US); Russell W. Koch, Hartville, OH (US); William L. Hergenrother, Akron, OH (US); Shunji Araki, Copley, OH (US)

(73) Assignee: Bridgestone Corporation, Tokyo (JP)

( * ) Notice: Subject to any disclaimer, the term of this patent is extended or adjusted under 35 U.S.C. 154(b) by 299 days.

(21) Appl. No.: 10/969,573

(22) Filed: Oct. 20, 2004

(65) Prior Publication Data

US 2006/0084730 A1 Apr. 20, 2006

(51) Int. Cl.
*C07D 249/16* (2006.01)
*C08K 9/00* (2006.01)
*C08F 36/00* (2006.01)

(52) U.S. Cl. .................. 548/257; 548/146; 523/215; 524/93; 525/329.3

(58) Field of Classification Search ........... 548/257, 548/146; 523/215; 524/93; 525/329.3
See application file for complete search history.

(56) References Cited

U.S. PATENT DOCUMENTS

| | | | |
|---|---|---|---|
| 4,557,306 A | 12/1985 | Graves | 152/548 |
| 4,570,690 A | 2/1986 | Graves | 152/564 |
| 4,751,271 A | 6/1988 | Graves | 525/229.2 |
| 4,761,446 A | 8/1988 | Graves et al. | 524/93 |
| 4,762,870 A | 8/1988 | Graves et al. | 524/93 |
| 4,778,857 A | 10/1988 | Graves et al. | 525/375 |
| 4,788,229 A | 11/1988 | Bohm et al. | 523/215 |
| 4,822,845 A | 4/1989 | Graves et al. | 524/519 |
| 5,001,171 A | 3/1991 | Bohm et al. | 523/206 |
| 5,091,449 A | 2/1992 | Cantillo et al. | 524/100 |
| 5,109,055 A | 4/1992 | Nagasaki et al. | 524/571 |
| 5,962,683 A | 10/1999 | Steinmann et al. | 544/180 |
| 6,596,798 B1 | 7/2003 | Rademacher et al. | 524/372 |
| 7,091,298 B2 * | 8/2006 | Schindler et al. | 528/34 |
| 7,098,260 B2 * | 8/2006 | Belin et al. | 524/83 |
| 7,112,634 B2 * | 9/2006 | Satsu et al. | 525/342 |
| 7,115,696 B2 * | 10/2006 | Roesler et al. | 528/28 |
| 7,119,150 B2 * | 10/2006 | Lin et al. | 525/332.6 |
| 7,120,326 B2 * | 10/2006 | Nakada et al. | 385/14 |
| 2003/0191225 A1 | 10/2003 | Tardivat et al. | 524/492 |
| 2004/0051210 A1 | 3/2004 | Tardivat et al. | 264/349 |

OTHER PUBLICATIONS

Fry, Edward M. Oxazoline Ring-Opening. J. Org. Chem. 15: 802-806 (1950).
Wiley, Richard H. and Leonard L. Bennett, Jr. The Chemistry of Oxazolines. Chemical Reviews v. 44, 447-476.

* cited by examiner

*Primary Examiner*—Deborah C. Lambkin
(74) *Attorney, Agent, or Firm*—Jenny Sheaffer; Meredith Hooker

(57) ABSTRACT

Dispersion of filler(s) in polymeric compositions are improved by the use of a polymer-filler coupling compound, Q—A—B, wherein Q comprises a dipolar nitrogen-containing moiety that can form a 1,3 dipolar addition to an unsaturated carbon-carbon bond; B is an oxazoline, thiazoline, alkoxysilane or allyltin moiety, and A is a linking atom or group that forms a bridge between Q and B.

68 Claims, 1 Drawing Sheet

POLYMER-FILLER COUPLING ADDITIVES

BACKGROUND

Figure 1:
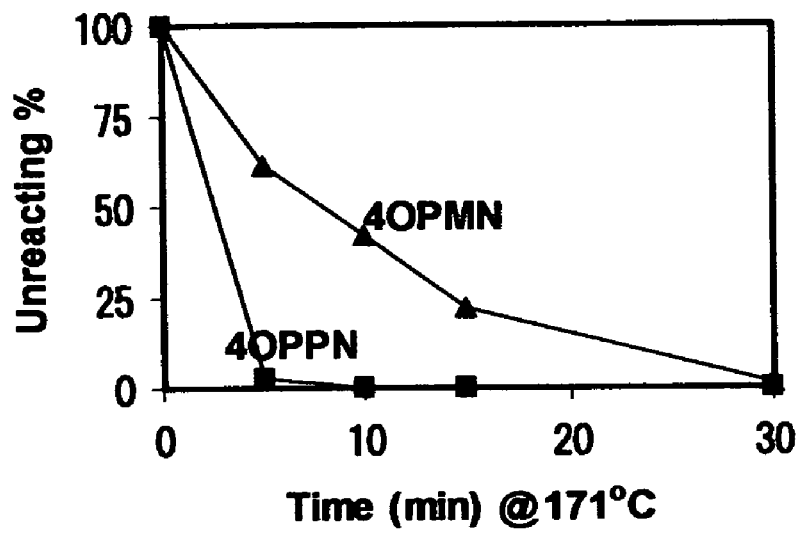

This invention generally relates to the dispersion of filler(s) in polymeric compounds and, in particular, to the preparation of low hysteresis rubber.

In many industries, it is often desirable to produce polymeric compounds in which fillers are well dispersed. In the rubber industry it can be desirable to produce elastomeric compounds exhibiting reduced hysteresis when compounded with other ingredients, such as reinforcing fillers, and then vulcanized. The hysteresis of a rubber refers to the difference between the energy applied to deform the rubber and the energy recovered as the rubber returns to its initial, undeformed state. Interaction between the elastomer molecules and the reinforcing filler(s) is known to affect hysteresis, and it has been recognized that hysteresis and other physical properties of compounded elastomer systems can be improved by ensuring good dispersion of the reinforcing filler throughout the elastomer component. Elastomeric compounds exhibiting reduced hysteresis, when fabricated into components for constructing articles such as tires, power belts, and the like, will manifest properties of increased rebound and reduced heat build-up when subjected to mechanical stress during normal use. In pneumatic tires, lowered hysteresis properties are associated with reduced rolling resistance and heat build-up during operation of the tire. As a result, lower fuel consumption is realized in vehicles using such pneumatic tires.

Carbon black and/or silica are well known reinforcing fillers in rubber compounds and these, as well as other fillers, are often used as fillers for polymeric compounds in other industries, such as in thermoplastics, composites, paint, and the like. In rubber, attempts at improving filler dispersion have included high temperature mixing of carbon black-rubber mixtures in the presence of selectively-reactive promoters to promote compounding material reinforcement. Other approaches have, for example, included surface oxidation of the compounding materials or chemical modifications to the terminal end of polymers using, for example, N,N,N',N'-tetramethyldiamino-benzophenone (Michler's ketone), tin coupling agents, and the like. All of these approaches have focused upon increased interaction between the elastomer and carbon black compounding materials resulting in stabilized dispersion of individual carbon black aggregates and a reduction in interaggregate contacts.

Dispersion of silica filler has been of concern because polar silanol groups on the surface of the silica particles tend to self-associate, leading to reagglomeration of the silica particles after compounding, poor silica dispersion and a high compound viscosity. The strong silica filler network results in a rigid uncured compound that is difficult to process in extrusion and forming operations. It has been recognized that improved silica dispersion can be achieved by the use during compounding, of bifunctional silica coupling agents having a moiety, such as a silyl group, reactive with the silica surface, and a moiety, such as a mercapto, amino, vinyl, epoxy or sulfur group, that binds to the elastomer. Improved silica dispersion has also been achieved by the use of elastomers that have been chemically modified at the chain end with functional groups, such as alkoxysilyl groups and the like, that chemically bind and/or interact with silica to improve dispersion.

However, there is still a need for improving dispersion of fillers in polymeric compositions, especially in the rubber industry to produce rubbers having low hysteresis properties and improved processability.

SUMMARY

Unexpectedly, it has been discovered that dispersion of filler(s) in polymeric compositions can be improved by the use of a polymer-filler coupling compound comprising a first moiety, Q, that can bind to a polymer by adding to unsaturated carbon-carbon bonds in the molecular structure of the polymer, a second moiety, B, that can bind to a surface group(s) on the filler(s), and a linking atom or group, A, that forms a bridge between Q and B. Moreover, it has been discovered that the use of the coupling compound as an additive in rubber compositions results in an increase in bound rubber and a reduced Payne effect and reduced tangent delta (tan δ), both indicators of reduced hysteresis in rubber compounds and articles made from them. The polymer-filler coupling compounds of the invention offer the advantage that a significant reduction in hysteresis can be obtained when using individual unsaturated elastomers in rubber compositions, as well as when using blends of rubbers that include unsaturated elastomers, and normal rubber mixing procedures.

In particular, a compound according to the invention has the formula Q—A—B, wherein Q comprises a dipolar nitrogen-containing moiety that can form a 1,3 dipolar addition to an unsaturated carbon-carbon bond; B is selected from the group consisting of an oxazoline moiety, a thiazoline moiety, an alkoxysilane moiety and an allyltin moiety; and A is a linking atom or group that forms a bridge between Q and B.

Q is preferably selected from the group of moieties consisting of a nitrone, a nitrile oxide and a nitrilimine. Such moieties can add to unsaturated carbon-carbon bonds in the molecular structure of a polymer. The B moiety of the compound Q—A—B is available to bind to a reactive surface group(s) on the filler aggregate and/or particle. Thus, the compound Q—A—B can promote filler dispersion by binding filler aggregates and/or particles along the entire molecular structure of the polymer (e.g., the polymer backbone and/or pendant groups).

Fillers that are useful in embodiments of the invention include, but are not limited to, carbon black, silica, and mineral fillers such as silicates, talc, kaolin, clay, metal oxides, aluminum hydrate, mica, and the like, and mixtures of any of the foregoing.

In embodiments according to the invention, the compound Q—A—B is employed in methods to promote filler dispersion in polymeric compositions, and to produce modified polymers in which the Q moiety of Q—A—B has added to unsaturated carbon-carbon bonds in the polymeric molecular structure. Further embodiments include, but are not limited to, rubber compositions and/or vulcanizates comprising an elastomer having unsaturated carbon-carbon bonds in its molecular structure, the compound Q—A—B, a filler having a surface moiety that is reactive with the B moiety of Q—A—B, and a cure agent. The embodiments further include a tire comprising at least one component, preferably a tire tread, that contains a vulcanizate according to embodiments of the invention.

The Q—A—B compound may also be useful as a bioactive agent, particularly in pharmaceutical compositions.

DETAILED DESCRIPTION

The terms elastomer, polymer and rubber are used interchangeably herein.

A compound that is particularly useful for promoting filler dispersion in a polymeric composition that comprises a polymer having unsaturated carbon-carbon bonds in its molecular structure has the formula Q—A—B, where Q comprises a dipolar nitrogen-containing moiety that can form a 1,3 dipolar addition to an unsaturated carbon-carbon bond, B is selected from the group consisting of an oxazoline moiety, a thiazoline moiety, an alkoxysilane moiety and an allyltin moiety; and A is a linking atom or group that forms a bridge between Q and B.

In addition to its use for promoting filler dispersion, the compound may have other uses. For example, it is known that nitrone-containing compounds such as, but not limited to, N-tert-butyl-alpha-phenylnitrone (PBN), are free-radical spin-trapping agents that can act as antioxidants in many biological systems. As a non-limiting example, administration of PBN can prevent oxidative damage to lipids and proteins of the liver and liver damage in experimental cirrhosis, and can protect against ischemic brain injury. Moreover, it is known that thiazole compounds and/or their derivatives can possess immuno-modulating activity and angiogenesis inhibiting activity. Therefore, the Q—A—B compound may be useful as a bioactive agent, particularly in pharmaceutical compositions, especially, but not limited to, a compound where Q comprises a nitrone moiety and/or B comprises a thiazoline moiety or a derivative thereof.

When used in this specification, the terms oxazoline moiety and thiazoline moiety are intended to include the structures embodied by one or more of the following formulas I—II

I-III:

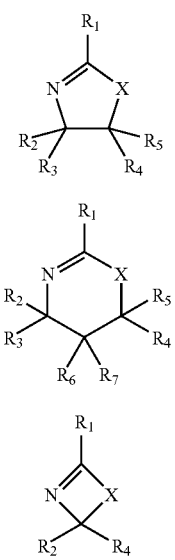

where X is oxygen or sulfur; and $R_1$–$R_7$ are independently selected from the group consisting of hydrogen, a branched or linear $C_1$–$C_{20}$ alkyl group, a branched or linear $C_3$–$C_{20}$ cycloalkyl group, a branched or linear $C_6$–$C_{20}$ aryl group, a branched or linear $C_7$–$C_{20}$ alkylaryl group, and A; and A is a linking atom or group that forms a bridge between Q and B.

Preferably, Q comprises nitrone, a nitrile oxide or a nitrilimine. More preferably, Q comprises a nitrone, a nitrile oxide or a nitrilimine having the formulas IV–VI, respectively:

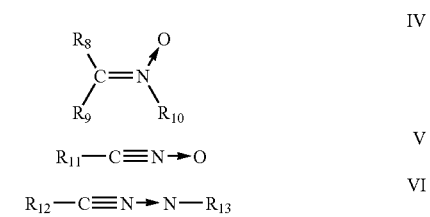

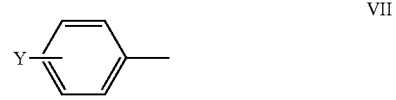

where $R_8$–$R_{13}$ are independently selected from the group consisting of A, hydrogen, a branched or linear $C_1$–$C_{20}$ alkyl group, a branched or linear $C_3$–$C_{20}$ cycloalkyl group, a branched or linear $C_6$–$C_{20}$ aryl group, a substituted phenyl group having the formula VII, where Y is selected from the group consisting of a nitro group, a cyano group, a chloro group, a bromo group, a branched or linear $C_1$–$C_{20}$ acyl group, a branched or linear $C_1$–$C_{20}$ alkoxycarbonyl group, a branched or linear $C_1$–$C_{20}$ alkoxy group, and a branched or linear $C_7$–$C_{20}$ alkylaryl group.

VII

The allyltin moiety preferably comprises the formula —CH=CHCH$_2$Sn(R$_{14}$)$_3$, wherein R$_{14}$ is independently selected from the group consisting of a branched or linear $C_1$–$C_{20}$ alkyl group, a branched or linear $C_3$–$C_{20}$ cycloalkyl group, a branched or linear $C_6$–$C_{20}$ aryl group and a branched or linear $C_7$–$C_{20}$ alkylaryl group. The —CH portion of the allyltin moiety binds to the A group of the compound.

The alkoxysilane moiety preferably comprises the formula —Si(OR$_{15}$)$_3$, wherein each R$_{15}$ independently contains one to about 6 carbon atoms, preferably one to about 4 carbon atoms, and the —Si portion of the alkoxysilane moiety binds to the A group of the compound.

The Linking atom or group A can be a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety. Further, A can comprise [A'-(Z-A")$_k$], where A' and A" are independently a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety; Z is oxygen, sulfur or C=O; and k is 1 to about 4. In a preferred embodiment, A comprises a phenyl group with an ortho, meta or para bond with Q and/or B. In another preferred embodiment, A comprises (CH$_2$)$_m$, where m is 1 to about 10.

As a non-Limiting example, one embodiment of the Q—A—B compound is illustrated as formula VII, 4-(2-oxazolyl)-phenyl-N-methyl-nitrone (4OPMN):

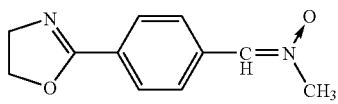

VIII

As a further non-limiting example, another embodiment of the Q—A—B compound is illustrated as formula VIII, 4-(2-oxazolyl)-phenyl-N-phenyl-nitrone (4OPPN):

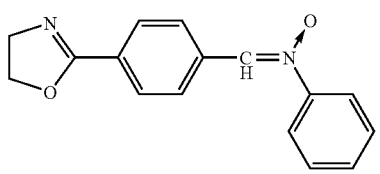

IX

Similarly, other non-limiting examples of the Q—A—B compound are 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and the like.

Ordinary chemical synthesis methods can be used to produce the exemplary compounds and other Q—A—B compounds without undue experimentation. Exemplary methods for producing 4OPPN and 4OPMN are disclosed in Examples 1 and 2, respectively, below. However, it is recognized that other known chemical synthesis methods, using other starting materials and intermediates, can also be used to produce these and other Q—A—B compounds. An exemplary method to produce a Q—A—B compound in which B is an allyltin moiety includes the following: an alkyltin lithium compound ($R_3SnLi$) is reacted with 1-bromo-4-chlorobut-2-ene (Cl—$CH_2$CH=CH$CH_2$—Br) to form $R_3$Sn—$CH_2$CH=CH$CH_2$—Cl (A). (A) is then reacted with lithium in the presence of tetrahydrofuran (THF) to produce $R_3$Sn—$CH_2$CH=CH$CH_2$—Li (B). (B) is then reacted with xylene dibromide (Br—$CH_2$-phenylene-$CH_2$—Br) to produce the mono adduct $R_3$Sn—$CH_2$CH=CH$CH_2$—$CH_2$-phenyl-$CH_2$—Br (C) with some diadduct and unreacted starting dibromo xylene. The product (C) is then separated out and reacted with hexamethylene tetraamine and acid to give $R_3$Sn—$CH_2$CH=CH$CH_2$—$CH_2$-phenyl-CH=O (D). (D) is then reacted with $NH_2$OH to produce a nitrile oxide (E), or with RNHOH to produce a nitrone (F). An exemplary method to produce a Q—A—B compound in which B moiety is an alkoysilane moiety can employ the compounds (E) or (F) obtained above. For example, the silane is formed from either (E) or (F) by reaction of the allyltin with excess $SiCl_4$ and then treatment of the respective product with alcohol ROH to give a trialkoxy siloxane-nitrile oxide or -nitrone. In each of these exemplary routes, A is $CH_2$ and each of the B moieties contains an attached allyl group. As stated above, it is recognized that synthesis of the above compounds is only exemplary and is not limited, as other known chemical synthesis methods, using other starting materials and intermediates, can also be used to produce these and other Q—A—B compounds.

The polymers used herein contain carbon-carbon unsaturation in their molecular structure and include thermoplastic polymers as well as thermosetting polymers. The unsaturation can be present along the polymer backbone and/or be present as a pendant group, such as an ethylenic group and the like. Suitable elastomers containing carbon-carbon unsaturation in their molecular structure include natural as well as synthetic rubbers, such as those produced by polymerizing aliphatic, conjugated diolefins, especially those containing 4 to 8 carbon atoms per molecule such as, but not limited to, butadiene, isoprene, pentadienes, and the like, or the copolymers and terpolymers of such dienes. The polymer backbones of the elastomers used herein preferably contain a significant amount of unsaturation. Preferably, at least about 5% of the carbon-carbon bonds in the polymer backbones are unsaturated bonds.

Characterization of rubber as having unsaturated carbon chains is well known in the art as shown by ANSI/ASTM Standard D 1418-79A where unsaturated-chain rubbers are referred to as R rubbers. Class R rubbers include natural rubber and various synthetic rubbers derived at least partly from diolefins. The following is a non-exclusive list of R class rubbers that can be used in the compositions of the present invention: acrylate-butadiene rubber; butadiene rubber; chloro-isobutene-isoprene rubber; chloroprene rubber; isoprene, synthetic; nitrile-butadiene rubber; nitrile-chloroprene rubber; nitrile-isoprene rubber; natural rubber, styrene-butadiene rubber; styrene-chloroprene rubber; and styrene-isoprene rubbers. The rubbers used herein having carbon-carbon unsaturation also can be other than the R rubbers such as, but not limited to, EDPM rubber derived from ethylene-propylenediene monomer, and typically having about 3% to about 8% of their carbon bonds as unsaturated carbon-carbon bonds.

Further representative of synthetic polymers for use in the embodiments of the invention include, but are not limited to, the homopolymerization products of butadiene and its homologues and derivatives as, for example, methyl butadiene, dimethyl butadiene and pentadienes as well as copolymers such as those formed from a butadiene or its homologues or derivatives with other unsaturated organic compounds. Among the latter are olefins, for example, ethylene, propylene or isobutylene which copolymerizes with isoprene to form polyisobutylene also known as butyl rubber; vinyl compounds which can copolymerize with diene monomers such as butadiene and isoprene; acrylic acid, acrylonitrile, methacrylonitrile, methacrylic acid, alpha methyl styrene, (o-, m-, or p-) methyl styrene and styrene, the latter compound polymerizing with butadiene to form styrene-butadiene rubber, as well as vinyl esters and various unsaturated aldehydes, ketones and ethers, such as acrolein and vinylethyl ether, and the like.

In general, the preferred elastomers are homopolymers of conjugated diene monomers, and copolymers and terpolymers of the conjugated diene monomers with monovinyl aromatic monomers and trienes. More preferably, elastomers for use in the present embodiments include natural rubber, synthetic polyisoprene, polybutadiene, polystyrene, styrene-butadiene copolymers, isoprene-butadiene copolymers, isoprene-styrene copolymers, terpolymers of styrene-isoprene-butadiene, acrylonitrile-butadiene rubber, terpolymers of acrylonitrile, butadiene and styrene, and blends thereof.

The chemical reaction between the compound Q—A—B and a polymer that contains unsaturated carbon-carbon bonds in its molecular structure is illustrated in Schemes 1–3. In each of these three schemes, the polymer (P) is represented as having "n" unsaturated carbon-carbon bonds that react with the Q moieties of "n" moles of Q—A—B. It is recognized from a practical standpoint that not all available unsaturated carbon-carbon bonds in the polymeric molecular structure will react and, therefore, "n" is meant to represent an average number of reactive sites. In Scheme 1, the Q moiety is a nitrone; in Scheme 2, the Q moiety is a nitrile oxide; and in Scheme 3, the Q moiety is a nitrilimine. For convenience, the modified polymers produced by reacting Q—A—B with P are illustrated as P-(Q'—A—B)$_n$; P-(Q"—A—B)$_n$; and P-(Q'"—A—B)$_n$, respectively, where Q', Q" and Q'" represent the reaction products of the respectively identified Q moiety with the polymer P.

Schemes 4–17 illustrate the second reaction, i.e., the binding of the B moiety of Q—A—B to a reactive group on the surface of the filler. This reaction occurs independently of the reaction of Q with the polymer P. That is, it is not necessary for the Q moiety to be bound to the polymer P in order for the B moiety-filler reaction to occur. The B moiety-filler reaction can occur prior to, at the same time as, or after the Q moiety-P reaction. However, for convenience, to illustrate how the polymer and filler can be coupled, Schemes 4–17 illustrate an embodiment in which the polymer has been modified prior to the reaction with the filler. The exemplary modified polymer is illustrated as that resulting from the reaction described in Scheme 1.

As illustrated in Schemes 4–11, the B moiety of Q—A—B comprises an oxazoline or thiazoline moiety that is reactive with surface groups of carbon black (CB), such that mixing Q—A—B with the carbon black allows for the direct binding of carbon black to the B moiety of the compound. Thus, the filler is bound along the molecular structure of the polymer by the reaction of Q with the polymer.

As illustrated in Schemes 12–15, the B moiety of Q—A—B comprises an oxazoline or thiazoline moiety that is reactive with the surface hydroxyl groups on the silica, such that mixing Q—A—B with silica filler allows for the direct binding of silica to the B moiety of the compound and the binding of the silica filler along the molecular structure of the polymer by the reaction of Q with the polymer.

As illustrated in Scheme 16, the B moiety of Q—A—B comprises an alkoxysilane group that is reactive with the surface hydroxyl groups on the silica, such that mixing Q—A—B with silica filler allows for the direct binding of silica to the B moiety of the compound and the binding of the silica filler along the molecular structure of the polymer by the reaction of Q with the polymer.

As illustrated in Scheme 17, the B moiety of Q—A—B comprises an allyltin group that is reactive with the surface ortho-quinone structures present on carbon black, such that mixing Q—A—B with carbon black filler allows for the direct binding of carbon black to the B moiety of the compound and the binding of the carbon black filler along the molecular structure of the polymer by the reaction of Q with the polymer.

In all the reactions illustrated above, more than one Q—A—B compound can be bound to surface groups on the filler particle or aggregate. This embodiment is particularly illustrated in Scheme 16.

When mixtures of carbon black and silica fillers are employed, the reactions will occur independently.

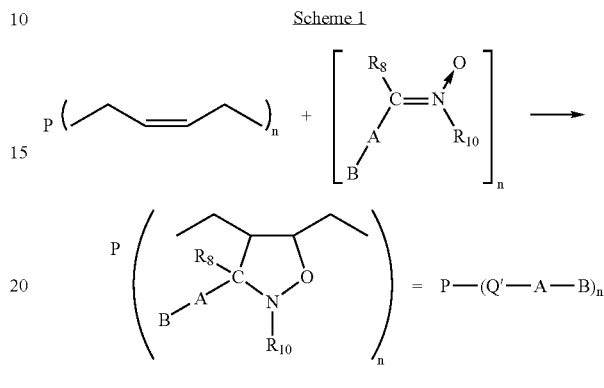

Scheme 5
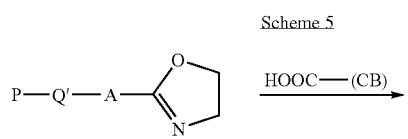
Scheme 6
Scheme 7
Scheme 8
Scheme 9
Scheme 10
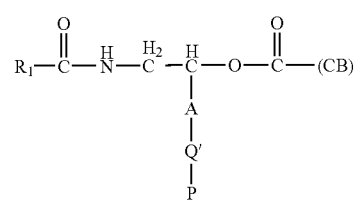
Scheme 11
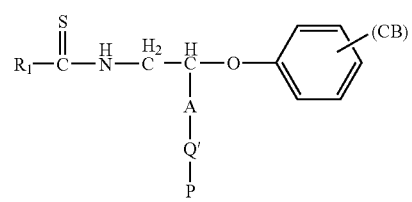
Scheme 12
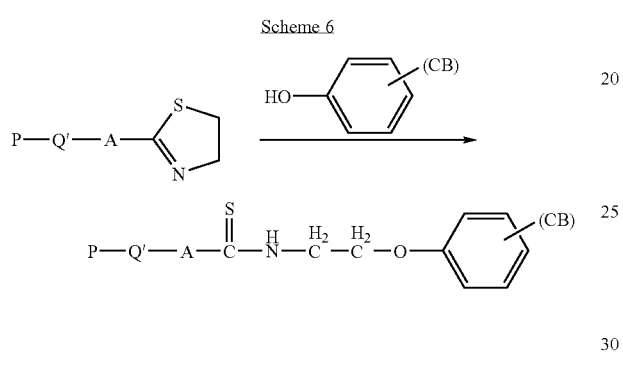

Scheme 13

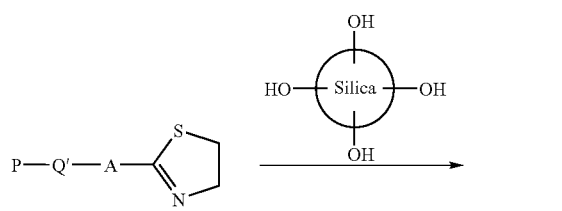

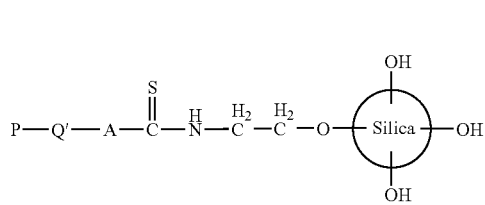

Scheme 14

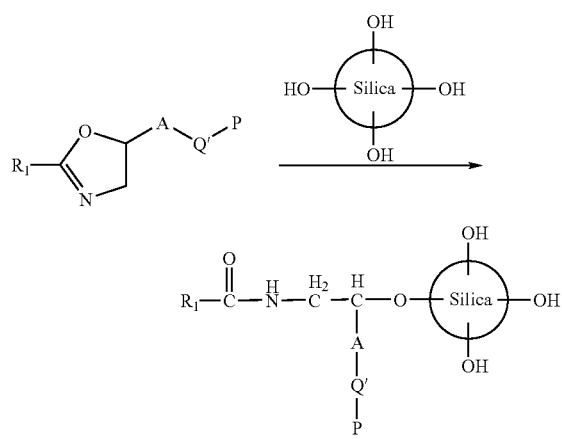

Scheme 15

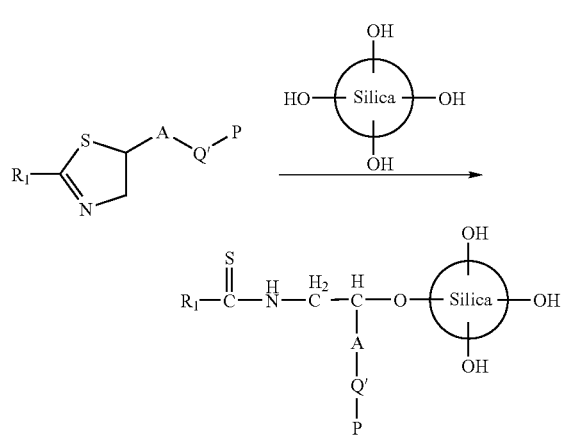

Scheme 16

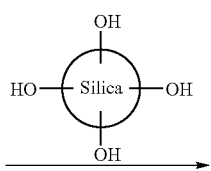

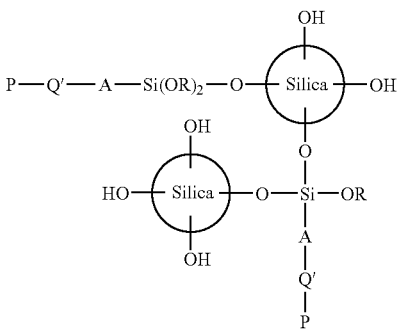

Scheme 17

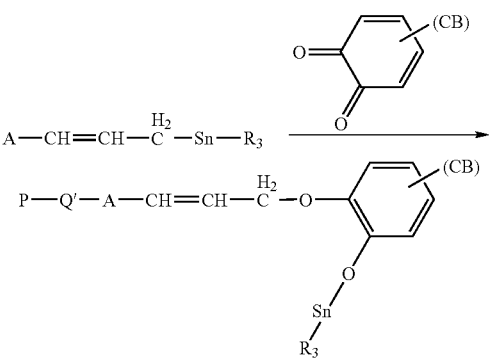

Although the reactions with carbon black and silica are illustrated in the schemes above, other fillers with surface groups reactive with the B moiety of Q—A—B will be bound along the molecular structure of the polymer by the reaction of Q with the polymer. For example, mineral fillers such as, but not limited to, silicates, talc, kaolin, clay, metal oxides, aluminum hydrate, mica, and the like, have such reactive surface groups, and these can be employed individually or in mixtures containing any of these, including mixtures with carbon black and/or silica.

As illustrated in Schemes 1–3 above, in one embodiment of the invention a modified polymer can be produced by contacting a polymer containing unsaturated carbon-carbon bonds in its molecular structure with a compound having the formula Q—A—B, as described above, to form a modified polymer. The amount of the Q—A—B compound can range from about 0.1 to about 30 percent by weight calculated on the weight of the polymer to be modified. Preferably, about 0.5 to about 10 percent by weight of the polymer is used, with a range of about 1 to about 8 percent by weight of the polymer being most preferred. The modification reaction can be conducted in solution, or under solvent-free conditions (solid state reaction). Preferably the reaction is conducted in the solid state. The Q—A—B compound can be added to the rubbers by any conventional technique, such as milling or in a Banbury mixer.

For example, a modified polymer can be obtained at any time after polymerization, such as by addition of the Q—A—B compound to the cement obtained from polymerization, by spraying the compound onto the dried polymer crumb or by adding the compound to a polymeric composition with the polymer prior to adding the filler.

Thus, a method for promoting filler dispersion in a polymeric composition can comprise the steps of (a) modifying a polymer having unsaturated carbon-carbon bonds in its molecular structure by reacting the polymer with about 0.1 percent to about 30 percent by weight of said polymer of a compound having the formula Q—A—B to form a modified polymer, and (b) reacting the modified polymer with a filler comprising a surface group that can bind to the B moiety of the compound.

In another embodiment, a method for promoting filler dispersion in a polymeric composition can comprise the step of mixing together (i) a polymer having unsaturated carbon-carbon bonds in its molecular structure, (ii) about 0.1 percent to about 30 percent by weight of said polymer of a compound having the formula Q—A—B; and (iii) a filler comprising a surface group that can bind to the B moiety of the compound.

Vulcanizable elastomeric compositions according to the invention comprise an elastomer containing unsaturated carbon-carbon bonds in its molecular structure; a hysteresis-reducing amount of a compound having the formula Q—A—B, preferably about 0.1 to about 30 percent by weight of the elastomer; a filler comprising a surface group that can bind to the B moiety of the compound; and a cure agent. By cure agent is meant a cure package containing sulfur and accelerators commonly used in sulfur-vulcanizable rubber compositions. The filler is preferably carbon black, silica or a mixture of silica and carbon black. In one embodiment, the Q—A—B compound is added in the masterbatch containing the elastomer and the filler. In another embodiment, the Q—A—B compound can be pre-reacted with the elastomer to form a modified elastomer, as described above. In yet another embodiment, the Q—A—B compound can be reacted with the elastomer and the filler by adding it in a remill stage or final mixing stage.

Thus, a method for making a vulcanized elastomeric composition can comprise the steps of (a) mixing together (i) an elastomer containing unsaturated carbon-carbon bonds in its molecular structure, (ii) a filler selected from the group consisting of carbon black, silica, a mineral filler, and mixtures thereof, (iii) a compound having the formula Q—A—B, and (iv) a cure agent; and (b) curing the composition.

In another embodiment, a method for making a vulcanized elastomeric composition can comprise the steps of (a) mixing together (i) a modified elastomer prepared by reacting an elastomer having unsaturated carbon-carbon bonds in its molecular structure with about 0.1 percent to about 30 percent by weight of said polymer of a compound having the formula Q—A—B, (ii) a filler selected from the group consisting of carbon black, silica, a mineral filler, and mixtures thereof, and (iii) a cure agent; and (b) curing the composition.

The resulting vulcanizable elastomeric composition, after both the Q-polymer and B-filler reactions have occurred, comprises (a) the reaction product of (i) an elastomer having unsaturated carbon-carbon bonds in its molecular structure, (ii) a compound having the formula Q—A—B, and (iii) a filler comprising a surface group bound to the B moiety of the compound; and (b) a cure agent.

The preferred conjugated diene polymers, or copolymers or terpolymers of conjugated diene monomers and monovinyl aromatic monomers, can be utilized as 100 parts of the rubber in the treadstock compound, or they can be blended with any conventionally employed treadstock rubber which includes natural rubber, synthetic rubber and blends thereof. Such rubbers are well known to those skilled in the art and include, but are not limited to, acrylonitrile-butadiene rubber, silicone rubber, the fluoroelastomers, ethylene acrylic rubber, ethylene vinyl acetate copolymer, epichlorohydrin rubbers, chlorinated polyethylene rubbers, chlorosulfonated polyethylene rubbers, hydrogenated nitrile rubber, tetrafluoroethylene-propylene rubber and the like. When the vulcanizable elastomeric composition of the present invention is blended with conventional rubbers, the amounts can vary widely with a lower limit comprising about ten percent to 20 percent by weight of the total rubber. The minimum amount will depend primarily upon the physical properties desired.

The vulcanizable elastomeric composition is preferably compounded with reinforcing fillers, such as silica, carbon black or a mixture of silica and carbon black. Examples of silica fillers, which can be used in the vulcanible elastomeric composition of the invention, include wet silica (hydrated silicic acid), dry silica (anhydrous silicic acid), calcium silicate, and the like. Other suitable fillers include aluminum silicate, magnesium silicate, and the like. Among these, precipitated amorphous silicas are preferred. These silicas are so-called because they are produced by a chemical reaction in water, from which they are precipitated as ultrafine, spherical particles. These primary particles strongly associate into aggregates, which in turn combine less strongly into agglomerates. The surface area, as measured by the BET method gives the best measure of the reinforcing character of different silicas. For silicas of interest for the present invention, the surface area should be about 32 $m^2/g$ to about 400 $m^2/g$, with the range of about 100 $m^2/g$ to about 250 $m^2/g$ being preferred, and the range of about 150 $m^2/g$ to about 220 $m^2/g$ being most preferred. The pH of the silica filler is generally about 5.5 to about 7 or slightly over, preferably about 5.5 to about 6.8.

Silica can be employed in the amount of 0 to about 100 parts per hundred parts of the elastomer (phr), preferably in an amount of about 5 to about 80 phr and, more preferably, in an amount of about 30 to about 80 phr. The useful upper range is limited by the high viscosity imparted by fillers of this type. Some of the commercially available silicas which can be used include, but are not limited to, Hi-Sil® 190, Hi-Sil® 210, Hi-Sil® 215, Hi-Sil® 233, Hi-Sil® 243, and the like, produced by PPG Industries (Pittsburgh, Pa.). A number of useful commercial grades of other silicas are also available from DeGussa Corporation (e.g., VN2, VN3), Rhone Poulenc (e.g., Zeosil® 1165MP), and J.M. Huber Corporation.

The elastomers can be compounded with all forms of carbon black. The carbon black can be present in amounts ranging from about 0 phr to about 100 phr. Preferably, carbon black is compounded at about 5 to about 80 phr and, more preferably, from about 20 to about 70 phr. The carbon blacks can include any of the commonly available, commercially-produced carbon blacks but those having a surface area of at least 20 $m^2/g$ and more preferably at least 35 $m^2/g$ up to 200 $m^2/g$ or higher are preferred. Surface area values are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks that can be used include acetylene blacks. Typical carbon blacks that are used include N110, N121, N220, N231, N242, N293, N299, N326, N330, N332, N339, N343, N347, N351, N358, N375, N472, N539, N472, N539, N550, N660, N683, N754, and N765. Depending on the particular use of the compound, the appropriate carbon black can be selected. Mixtures of two or more of the above blacks can be used in preparing products of this invention. The carbon blacks utilized in the preparation of the filled vulcanizates of the invention can be in pelletized form or an unpelletized flocculant mass. Preferably, for more uniform mixing, unpelletized carbon black is employed.

The vulcanizable elastomeric compositions can also contain additional processing additives such as, but not limited to, silica coupling agents, silica hydrophobating agents, and the like, in addition to other conventional rubber additives including, for example, additional fillers, plasticizers, antioxidants, activators, retarders, accelerators, pigments, cure agents, processing additives such as oils and resins, including tackifying resins, pigments, fatty acid, zinc oxide, waxes, antioxidants, anti-ozonants, and peptizing agents. As known to those skilled in the art, depending on the intended use of the sulfur vulcanizable and sulfur vulcanized material (rubbers), the additives mentioned above are selected and commonly used in conventional amounts, using standard rubber mixing equipment and procedures. Such elastomeric compositions, when vulcanized using conventional rubber vulcanization conditions, exhibit reduced hysteresis, which means a product having increased rebound, decreased rolling resistance and lessened heat build-up when subjected to mechanical stress. Products including tires, power belts and the like are envisioned. Decreased rolling resistance is, of course, a useful property for pneumatic tires, both radial as well as bias ply types and thus, the vulcanizable elastomeric compositions of the present invention can be utilized to form treadstocks for such tires. Pneumatic tires can be made according to the constructions disclosed in U.S. Pat. Nos. 5,866,171; 5,876,527; 5,931,211; and 5,971,046, the disclosures of which are incorporated herein by reference. The composition can also be used to form other elastomeric tire components such as subtreads, sidewalls, body ply skims, bead fillers and the like.

Thus, the embodiments of the invention include vulcanizates of the vulcanizable rubber compositions described above, and a tire comprising at least one component that comprises a vulcanized elastomeric composition that comprises the reaction product of an elastomer having unsaturated carbon-carbon bonds in its molecular structure, a filler selected from the group consisting of carbon black, silica, and mixtures thereof a cure agent, and a compound having the formula Q—A—B. Preferably, the tire component is a tire tread.

Typical amounts of tackifier resins, if used, comprise about 0.5 to about 10 phr, usually about one to about 5 phr. Typical amounts of compounding aids comprise about one to about 50 phr. Such compounding aids can include, for example, aromatic, naphthenic, and/or paraffinic processing oils.

Representative of the antidegradants that can be in the rubber composition include monophenols, bisphenols, thio-bisphenols, polyphenols, hydroquinone derivatives, phosphates, phosphate blends, thioesters, naphthylamines, diphenol amines as well as other diaryl amine derivatives, paraphenylene diamines, quinolines and blended amines. Antidegradants are generally used in an amount ranging from about 0.1 phr to about 10 phr with a range of from about 0.5 to 6 phr being preferred. For example, typical amounts of antioxidants comprise about 0.1 to about 5 phr. Representative antioxidants can be, for example diphenyl-p-phenylenediamine and others, such as for example, those disclosed in the *Vanderbilt Rubber Handbook* (1978), pages 344 to 346. Typical amounts of anti-ozonants can comprise about 0.1 to about 5 phr.

Typical amounts of fatty acids, if used, which can include stearic acid, palmitic acid, linoleic acid or a mixture of one or more fatty acids, can comprise about 0.5 to about 3 phr. Typical amounts of waxes comprise about one to about 2 phr. Often microcrystalline waxes are used. Typical amounts of peptizers, if used, comprise about 0.1 to about 1 phr. Typical peptizers can be, for example, pentachlorothiophenol and dibenzamidodiphenyl disulfide. Pentachlorophenol can be used, for example, in an amount ranging from about 0.1 phr to 0.4 phr with a range of from about 0.2 to 0.3 phr being preferred.

Representative of processing oils which can be used in the rubber composition of the present invention include aliphatic-naphthenic aromatic resins, polyethylene glycol, petroleum oils, ester plasticizers, vulcanized vegetable oils, pine tar, phenolic resins, petroleum resins, polymeric esters and resins. These processing oils can be used in a conventional amount ranging from about 0 to about 50 phr with a range of from about 5 to 25 phr being preferred.

It is readily understood by those having skill in the art that the rubber composition would be compounded by methods generally known in the rubber compounding art, such as mixing the various vulcanizable polymer(s) with various commonly used additive materials such as, for example, curing agents, activators, retarders, accelerators, and the like.

The reinforced rubber compounds can be cured in a conventional manner with known vulcanizing agents, such as such as sulfur and accelerators. Modification of polymers and filler binding according to the present invention does not appreciably affect cure times and, thus, the rubber compounds can be cured for a conventional amount of time. When a vulcanizing agent is used, the amount of the agent used is 0.1 to 5 parts by weight, preferably 0.1 to 3 parts by weight, based on 100 parts by weight of the rubber material with a range of from about 0.1 phr to about 2 phr being preferred. Vulcanizing agents can be used alone or in combination. Cured or cross-linked polymers will be referred to as vulcanizates for purposes of this disclosure. For a general disclosure of suitable vulcanizing agents, one can refer to Kirk-Othmer, *Encyclopedia of Chemical Technology*, 3rd ed., Wiley Interscience, N.Y. 1982, Vol. 20, pp. 365 to 468, particularly "Vulcanization Agents and Auxiliary Materials," pp. 390 to 402.

Zinc oxide and stearic acid are conventionally used to vulcanize elastomers. Zinc oxide is generally used in a conventional amount ranging from about 0.5 to about 5 phr.

Stearic acid is generally used in a conventional amount ranging from about 1 to about 4 phr.

The vulcanization is conducted in the presence of a sulfur vulcanizing agent. Examples of suitable sulfur vulcanizing agents include "rubbermaker's" soluble sulfur; sulfur donating vulcanizing agents, such as an amine disulfide, polymeric polysulfide or sulfur olefin adducts; and insoluble polymeric sulfur. Preferably, the sulfur vulcanizing agent is soluble sulfur or a mixture of soluble and insoluble polymeric sulfur. The sulfur vulcanizing agents are used in an amount ranging from about 0.1 to about 10 phr, more preferably about 1.5 to about 5 phr, with a range of about 1.5 to about 3.5 phr being most preferred.

Accelerators are used to control the time and/or temperature required for vulcanization and to improve properties of the vulcanizate. The vulcanization accelerators used in the present invention are not particularly limited. Representative of conventional accelerators are amines, guanidines, thioureas, thiols, thiurams, sulfonamides, dithiocarbamates and xanthates which are typically added in amounts of from about 0.2 to about 10 phr, with a range of from about 2 phr to about 5 phr being preferred. Examples include thiazol vulcanization accelerators, such as 2-mercaptobenzothiazol, dibenzothiazyl disulfide, N-cyclohexyl-2-benzothiazyl-sulfenamide (CBS), N-tert-butyl-2-benzothiazyl sulfenamide (TBBS), and the like; and guanidine vulcanization accelerators, such as diphenylguanidine (DPG) and the like. The amount of the vulcanization accelerator used is about 0.1 to about 5 phr, preferably about 0.2 to about 3 phr.

The vulcanizable elastomeric composition of the present invention can be obtained by milling the components by using a milling apparatus, such as a mill, an internal mixer, and the like for a sufficient time and at a high enough temperature to achieve the desired physical properties of the resulting compound. The mixing of the vulcanizable elastomeric composition can be accomplished by methods known to those having skill in the rubber mixing art. For example, the ingredients can be mixed in two or more stages, consisting of at least a "master batch" stage (comprising mixing of the elastomer, with at least a portion of the carbon black and/or silica and other ingredients); and a "final stage", in which the cure agents are typically added. There can also be a mixing stage in which the mixture is re-milled without the addition of ingredients. The Q—A—B compound can be added in any stage of the mixing process.

The mixing temperature can vary from stage to stage. However, for purposes of the invention, the Q—A—B compound, the elastomer and the filler can be mixed at a mixing temperature of about 60° C. to about 200° C., typically 90° C. to about 190° C. and, more preferably, about 120° C. to about 180° C. In one embodiment of the invention, a portion of the filler and/or the Q—A—B compound can be added to the elastomer in the master batch stage, and the remainder added to a remill stage.

EXAMPLES

The following examples illustrate the preparation of exemplary Q—A—B compounds and elastomeric compositions containing the compound. However, the examples are not intended to be limiting, as other methods for preparing the compound and the rubber compositions and different rubber compounding formulations can be employed without departing from the scope of the invention herein disclosed and claimed.

Example 1

Preparation of 4-(2-Oxazolyl)-Phenyl-N-Phenylnitrone (4OPPN)

To a stirred mixture of 15.0 gm 4-formyl-benzoylchloride (1 equivalent, eq.) in 300 ml chloroform, was added dropwise at −10° C., 10.9 gm of a solution of 2-aminoethanol (2 eq.) in chloroform (200 ml). After the addition, the resulting mixture was stirred at 25° C. for 2 hours and a resulting white precipitate was removed by filtration. The filtrate was then dried with a rotavapor and 17.4 gm of a yellow liquid, 4-formyl-N-(2-hydroxyethyl)-benzamide, was obtained.

Concentrated sulfuric acid (50 ml) was added dropwise with stirring to 4-formyl-N-(2-hydroxyethyl)-benzamide (17.4 gm) and the mixture was heated at 100° C. for one hour. The solution was added dropwise with stirring to a mixture of sodium hydroxide (20%, 500 ml) and chloroform (500 ml), the temperature being maintained by cooling below 15° C. The organic phase was then separated off and dried. 6.3 gm of 4-(2-oxazolyl)-benzaldehyde was collected.

A mixture of 4-(2-oxazolyl)-benzaldehyde (1 eq., 6.3 gm) and N-phenyl-hydroxyamine (1 eq., 3.9 gm) was refluxed in ethanol (100 ml) for 30 minutes and concentrated to a volume of 50 ml. An equal amount (50 ml) of water was added and the mixture was cooled in a refrigerator at 5° C. overnight. White crystals were obtained, which were isolated by filtration and dried, producing 6.7 gm of 4-(2-oxazolyl)-phenyl-N-phenylnitrone.

Example 2

Preparation of 4-(2-Oxazolyl)-Phenyl-N-Methylnitrone (4OPMN)

To a stirred mixture of 4-formyl-benzoylchloride (15.0 gm, 89 mmol) in chloroform (300 ml), was added dropwise at −10° C. a solution of 2-aminoethanol (10.9 gm, 178 mmol) in chloroform (200 ml). After the addition, resulting mixture was stirred at 25° C. for 2 hours and then a white precipitate was filtered. The filtrate was dried with a rotavapor and 17 gm (88 mmol) of yellow liquid, 4-formyl-N-(2-hydroxyethyl)-benzamide, was obtained. (99% yield)

Concentrated sulfuric acid (50 ml) was added dropwise with stirring to 4-formyl-N-(2-hydroxyethyl)-benzamide (17 gm, 88 mmol) and the mixture was heated at 100° C. for one hour. The solution was added dropwise with stirring to a mixture of sodium hydroxide (20%, 500 ml) and chloroform (500 ml), the temperature being maintained by cooling below 15° C. The organic phase was then separated off and dried. 6.3 gm (36 mMol) of 4-(2-oxazolyl)-benzaldehyde was collected. (41% yield)

The mixture of 4-(2-oxazolyl)-benzaldehyde (6.3 gm, 36 mmol) and N-methyl-hydroxyamine (1.7 gm, 36 mmol) was refluxed in ethanol (100 ml) for 30 minutes and concentrated to a volume of 50 ml. Then 50 ml of water was added and the mixture was cooled at 5° C. in a refrigerator overnight. White crystals were obtained, which were filtered and dried. 5.1 gm (25 mmol) of 4-(2-oxazolyl)-phenyl-N-methylnitrone was collected. (69% yield, overall 28% yield)

Example 3

The reactivity of 4OPPN and 4OPMN with a model unsaturated compound, cyclododecene, was determined. Briefly, each reactive compound was separately mixed with 1 ml cyclododecene (having a formula weight of 166.31 and a standard density of 0.863 g/ml) in the amounts listed in Table I, and heated at 171° C. The amount of each reactive compound recoverable at various time periods during the reaction with cyclododecene is an indication of the reactivity of each of the compound with unsaturated carbon-carbon bonds. A comparison of the reactivity of 4OPPN and 4OPMN with cyclododecene is illustrated in FIG. 1. Both 4OPPN and 4OPMN were reactive, and 4OPPN was determined to be more reactive than 4OPMN. These results show that both 4OPMN and 4OPPN have high reactivity with unsaturated carbon-carbon bonds.

TABLE 1

Reaction with Cyclododecene*

| Run No. | Reactive Compound | FW (g/mol) | Heating Time @ 170° C. (min) | Amount (mg) | Recovered (%) |
|---|---|---|---|---|---|
| 1 | 4OPPN | 266.28 | 0 | 5.56 | 100 |
| 2 | | | 5 | 5.52 | 3 |
| 3 | | | 10 | 5.60 | 0 |
| 4 | | | 15 | 5.65 | 0 |
| 5 | | | 30 | 5.60 | 0 |
| 6 | 4OPMN | 204.21 | 0 | 3.97 | 100 |
| 7 | | | 5 | 4.09 | 61.1 |
| 8 | | | 10 | 3.97 | 41.8 |
| 9 | | | 15 | 3.83 | 22 |
| 10 | | | 30 | 4.05 | 1.3 |

*All reactions were performed in 1 ml of cyclododecene having a formula weight (FW) of 166.31 g/mol and a standard density of 0.863 g/ml.

Example 4

To determine if the target property of reduced hysteresis was met, the value of tan delta (tan δ) measured at 5% strain using an ARES-A Rheometer at 50° C. and 15 Hz, and ΔG' (Payne effect) at 0.1 to 20% strain, were employed. The tan δ is a measure of the ratio of the loss modulus of the compound to the storage modulus and it has been found that the lower the magnitude of tan δ at 50° C., the lower is the hysteresis of the compound. To determine the effect of 4OPPN and 4OPMN compounds on the hysteresis properties of rubber, compounding formulations containing solution SBR and carbon black (N339, 50 phr) and other typical compounding ingredients such as those illustrated in Table II, were prepared. Varying, but equal molar amounts of 4OPPN and 4OPMN were respectively added to separate batches, as illustrated in Table III. For comparison, a commercially available additive (Sumifine® 1162, available from Sumitomo Chemical Company) known to reduce hysteresis in natural rubber and a hysteresis-reducing tin-functionalized solution SBR polymer, were also evaluated.

TABLE II

Compounding Formulation

| | C-1 (phr) | Stock 1 (phr) |
|---|---|---|
| Masterbatch | | |
| Polymer** | 120 | 120 |
| Carbon Black*** | 50 | 50 |
| Stearic Acid | 2 | 2 |
| 6PPD† | 1 | 1 |
| 4OPPN | | 2 |
| Final Batch | | |
| Zinc Oxide | 3 | 3 |
| DPG‡ | 0.5 | 0.5 |

TABLE II-continued

Compounding Formulation

| | C-1 (phr) | Stock 1 (phr) |
|---|---|---|
| MBTS‡ | 1 | 1 |
| Sulfur | 1.3 | 1.3 |

**Solution SBR 35% styrene, 14% Vinyl, 20 phr of aromatic oil.
***N339
†antioxidant N-(1,3-dimethylbutyl)-N'-phenyl-1,4-Benzenediamine
‡accelerators, diphenylguanidine (DPG) and Benzothiazyl Disulfide (MBTS).

Figure 2:
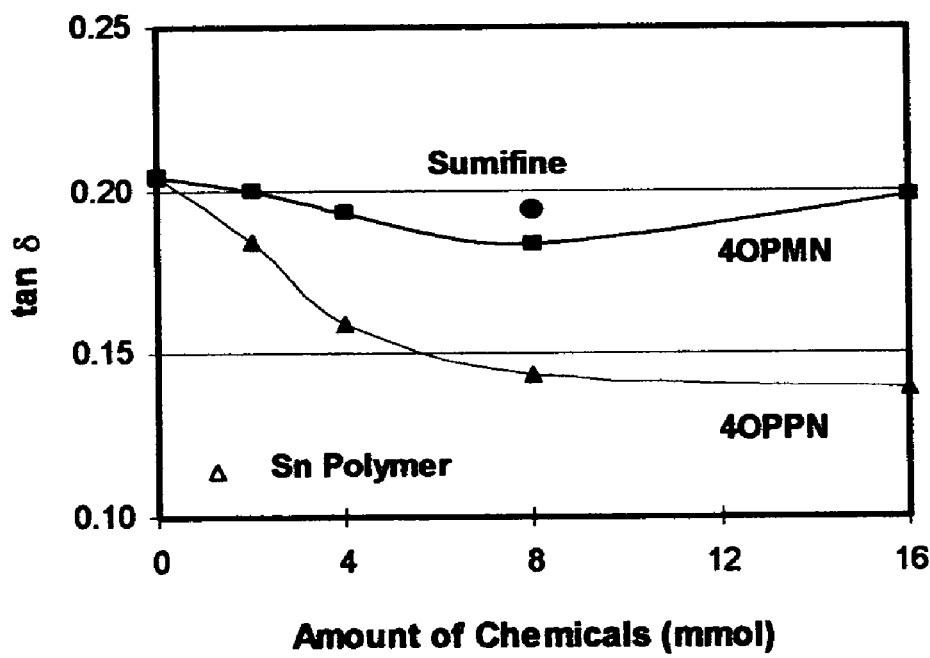

The results are illustrated in Table III and FIG. 2. Rubbers compounded with 4OPPN showed lower hysteresis (lower tan δ and ΔG') than those compounded with 4OPMN and Sumifine® 1162, but not as low as the terminally difunctional tin polymer. A lower tan δ @ 50° C. indicates improved rolling resistance in tire treads made from these stocks. Although the difunctional tin polymer gave a larger reduction in hysteresis, its use can require that a specific polymer molecular weight and composition be prepared in order to utilize the tin-functionalized technology. In contrast, the polymer-filler coupling compounds of the invention offer the advantage that a significant reduction of hysteresis can be obtained by using any unsaturated elastomer, including those employed in blends, and normal rubber mixing procedures. Without being bound by theory, it is believed that the higher the reactivity of an invention coupling compound with the polymer, the larger the hysteresis-reducing effect. The reduced hysteresis achieved with 4OPPN and 4OPMN reached a maximum with the use of about 2 phr (8 mMol) of 4OPPN and about 1.6 phr (8 mMol) of 4OPMN, respectively.

TABLE III

Comparison of Hysteresis Properties of Rubbers

| Compound | 0 mmol (phr) | 2 mmol (phr) | 4 mmol (phr) | 8 mmol (phr) | 16 mmol (phr) |
|---|---|---|---|---|---|
| 4OPPN | — | 0.53 | 1.07 | 2.13 | 4.26 |
| 4OPMN | — | 0.41 | 0.82 | 1.63 | 3.27 |
| Sumifine ® 1162$^a$ | — | — | — | 2.55 | — |
| Tin functionalized solution SBR$^b$ | 1.23 mmol | | | | |
| tan δ (50° C., 5% strain) | | | | | |
| No additive | 0.204 | | | | |
| 4OPPN | | 0.184 | 0.159 | 0.143 | 0.139 |
| 4OPMN | | 0.200 | 0.193 | 0.183 | 0.198 |
| Sumifine 1162 | | | | 0.194 | |
| Tin functionalized solution SBR$^b$ | 0.114 | | | | |
| ΔG' (0.1–20% strain) MPa | | | | | |
| No additive | 3.375 | | | | |
| 4OPPN | | 2.395 | 1.615 | 1.101 | 0.861 |
| 4OPMN | | 3.263 | 3.290 | 2.700 | 3.36 |
| Sumifine 1162 | | | | 5.15 | |
| Tin functionalized solution SBR$^b$ | 0.6 | | | | |

$^a$N,N'-di(2-nitro-2-methyl-propyl)-hexamethylenediamine, Sumitomo Rubber Industries
$^b$Solution SBR initiated with tributyltin-lithium and terminated with tributyltin chloride

Example 5

In order to demonstrate the preparation and properties of the vulcanizable elastomeric composition of the present invention, two further stocks of rubber were prepared using the compounding formulation shown in Table II. Stock 1 was prepared with the addition of 2 phr of 4OPPN to the elastomer/carbon black composition in the masterbatch. For comparison purposes, another stock (C-1) was prepared without the addition of 4OPPN. The final stocks were sheeted and subsequently molded at 171° C. for 15 minutes. The annealing conditions employed are similar to conventional curing conditions.

The green stocks (prior to annealing) were characterized as to Mooney viscosity, the percentage of bound rubber and cure characteristics. The Mooney viscosity measurement was conducted at 130° C. using a large rotor, and was recorded as the torque when rotor had rotated for 4 minutes. The sample was preheated at 130° C. for 1 minute before the rotor was started. The $t_{10}$ is the time required for the viscosity to increase by 10% of the final viscosity during a Mooney-scorch measurement. It is used as an index to predict how fast the compound viscosity will increase during processing (e.g., during extrusion). $t_{50}$ and $t_{90}$ are the times taken for a torque increase of 50% and 90%, respectively, of the total torque increase during the cure characterization test. A Monsanto Rheometer MD2000 was used to characterize the stock curing process.

As illustrated in Table IV, the stock containing the 4OPPN had a higher percentage of bound rubber than the comparison stock, indicating that more carbon black filler was bound to the polymer. The Mooney Viscosity and cure characteristics were not significantly different between the two stocks.

The tensile properties for the two cured stocks were measured using the standard procedure described in ASTM-D 412 at 25° C. The tensile test specimens were rings with a diameter of 0.05 inches and a thickness of 0.075 inches. A gauge length of 1.0 inch was used for calculating the tensile properties. As illustrated by the results of the tensile tests in Table IV, the stock containing 4OPPN showed equivalent mechanical strength to the comparison stock. The Payne effect (filler flocculation, ΔG') was measured using a frequency of 15 Hz over the strain region of 0.25 to 20% at 50° C. Stock 1 showed a significantly reduced tan δ, G' (loss modulus) and Payne effect (ΔG') compared to the C-1 stock not containing 4OPPN, resulting from coupling of the carbon black throughout the polymer molecular structure. Therefore, the addition of 4OPPN to the rubber composition resulted in a stock having better carbon black dispersion and lower hysteresis compared to a stock not containing 4OPPN.

TABLE IV

Rubber Properties

| | | C-1 | Stock 1 |
|---|---|---|---|
| Mooney Viscosity | ML1 + 4/130° C. | 69.4 | 65.0 |
| Bound Rubber (%) | | 39.3 | 48.0 |
| MDR 2000 | ML (kg-cm) | 2.50 | 2.15 |
| AT 171° C. | MH (kg-cm) | 13.4 | 11.75 |
| | t10 (min) | 0.92 | 0.80 |
| | t50 (min) | 1.39 | 1.19 |
| | t90 (min) | 2.48 | 2.42 |
| Micro Dumbell | M50 (MPa) | 0.97 | 1.06 |
| Tensile at room | M100 (MPa) | 1.52 | 1.724 |
| temperature | M200 (MPa) | 3.23 | 3.85 |
| (unaged | M300 (MPa) | 5.70 | 7.00 |
| rubber) | | | |
| | TB (MPa) | 23.20 | 25.67 |
| | EB (%) | 760 | 725 |
| | TF (MPa) | 73.66 | 77.98 |
| ARES-A at 50° C., 15 Hz | | | |
| 5% strain | G' (MPa) | 2.26 | 1.89 |
| | tan δ | 0.178 | 0.151 |
| | ΔG' [0.1–20% strain] (MPa) | 1.80 | 0.84 |

Example 6

In order to demonstrate further the preparation and properties of the vulcanizable elastomeric composition of the present invention, six stocks of rubbers were prepared using the compounding formulation and mixing conditions shown in Table V.

Stock 2 and comparison stocks C-2 and C-3 each contained carbon black and silica fillers in equal amounts (25 phr carbon black, 25 phr silica); whereas, stock 3 and comparison stocks C-4 and C-5 each contained silica as the only reinforcing filler (50 phr silica). Stocks 2 and 3 each contained the 4OPPN additive; comparison stocks C-2 and C-4 contained no additive; and comparison stocks C-3 and C-5 contained a polysulfide silica coupling agent, Si69. After compounding, the final stocks were sheeted and subsequently molded at 171° C. for 15 minutes.

The results of the testing of the rubber properties are illustrated in Table VI. The results show that the addition of a 4OPPN to the composition (stock 2) resulted in improved carbon black and silica dispersion, as determined by a lower Payne effect (ΔG') and reduced hysteresis, as determined by a lower tan δ. Although the Si69 was expected to improve the dispersion of the silica filler, the results obtained by the addition of 4OPPN were lower than the Si69 comparison compound C-3, illustrating that the 4OPPN improved the dispersion of the silica filler, as well as the carbon black filler.

A comparison of stock 3 with stock C-5 illustrates that the 4OPPN resulted in a lower tan δ, although the Si69-containing stock was more efficient in silica dispersion than the 4OPPN alone, as measured by the decrease in the Payne effect (ΔG').

TABLE V

Compounding Formulation

| | C-2 (phr) | C-3 (phr) | Stock 2 (phr) | C-4 (phr) | C-5 (phr) | Stock 3 (phr) |
|---|---|---|---|---|---|---|
| Masterbatch | | | | | | |
| Polymer** | 100 | 100 | 100 | 100 | 100 | 100 |
| Carbon Black*** | 25 | 25 | 25 | | | |
| Silica | 25 | 25 | 25 | 50 | 50 | 50 |
| Oil | 15 | 15 | 15 | 15 | 15 | 15 |
| Stearic Acid | 2 | 2 | 2 | 2 | 2 | 2 |

TABLE V-continued

Compounding Formulation

| | C-2 (phr) | C-3 (phr) | Stock 2 (phr) | C-4 (phr) | C-5 (phr) | Stock 3 (phr) |
|---|---|---|---|---|---|---|
| 6PPD† | 1 | 1 | 1 | 1 | 1 | 1 |
| Si69 | | 2 | | | 4.0 | |
| 4OPPN | | | 2.13 | | | 2.13 |
| Subtotal Final Batch | 168.00 | 170.00 | 170.13 | 168.00 | 172.00 | 170.13 |
| Zinc Oxide | 3 | 3 | 3 | 3 | 3 | 3 |
| DPG‡ | 0.5 | 0.5 | 0.5 | 0.5 | 0.5 | 0.5 |
| MBTS‡ | 1 | 1 | 1 | 1 | 1 | 1 |
| TBBS‡ | 0.5 | 0.5 | 0.5 | 1 | 1 | 1 |
| Sulfur | 1.3 | 1.3 | 1.3 | 1.3 | 1.3 | 1.3 |
| Total | 174.3 | 176.3 | 176.4 | 174.8 | 178.8 | 176.9 |

\*\*Solution SBR (35% styrene, 19% vinyl, $ML_{1+4}$ @ 100° C. = 52);
\*\*\*N339
†antioxidant, N-(1,3-dimethylbutyl)-N'-phenyl-1,4-benzenediamine
‡accelerators, diphenylguanidine (DPG), benzothiazyl disulfide (MBTS) and N-tert-2-benzothiazole sulfenamide (TBBS)

TABLE VI

Rubber Properties

| | | C-2 | C-3 | Stock 2 | C-4 | C-5 | Stock 3 |
|---|---|---|---|---|---|---|---|
| Mooney Viscosity | ML1 + 4/130° C. | 62 | 44 | 66 | 102 | 51 | 108 |
| Mooney Scorch Time TEST | minutes | 24.6 | 26.2 | 22.3 | 11.2 | 20.0 | 21.6 |
| Micro Dumbell | M50 (MPa) | 1.24 | 1.54 | 1.22 | 1.42 | 1.69 | 1.32 |
| Tensile at room | M100 (MPa) | 1.61 | 2.41 | 1.69 | 1.67 | 2.65 | 1.59 |
| temperature | M200 (MPa) | 2.57 | 4.49 | 2.87 | 2.37 | 4.72 | 2.30 |
| (unaged rubber) | M300 (MPa) | 3.70 | 7.01 | 4.30 | 3.15 | 7.15 | 3.12 |
| | TB (MPa) | 15.27 | 25.92 | 17.98 | 11.16 | 20.73 | 11.13 |
| | EB (%) | >1000 | 870 | >1000 | >1000 | 717 | >1000 |
| | TF (MPa) | 62.3 | 101.8 | 74.2 | 47.4 | 67.8 | 47.5 |
| ARES-A at 50° C., 15 Hz | | | | | | | |
| 5% strain | G' (MPa) | 3.41 | 3.18 | 3.05 | 8.15 | 4.41 | 6.98 |
| | tan δ | 0.200 | 0.195 | 0.173 | 0.107 | 0.143 | 0.120 |
| | ΔG' [0.1–20% strain] (MPa) | 3.66 | 3.21 | 2.04 | 6.29 | 3.92 | 5.40 |
| | Δ tan δ [0.1–20% strain] (MPa) | 0.101 | 0.098 | 0.064 | 0.097 | 0.069 | 0.087 |

In summary, the addition of exemplary Q—A—B compounds to rubber compositions results in improved filler dispersion and lowered hysteresis.

While the invention has been described herein with reference to the preferred embodiments, it is to be understood that it is not intended to limit the invention to the specific forms disclosed. On the contrary, it is intended that the invention cover all modifications and alternative forms falling within the scope of the appended claims.

We claim:

1. A compound having the formula Q—A—B, wherein:
Q comprises a dipolar nitrogen-containing moiety;
B is selected from the group consisting of an oxazoline moiety, a thiazoline moiety, an alkoxysilane moiety and an allyltin moiety; and
A is a linking atom or group that forms a bridge between Q and B.

2. The compound of claim 1, wherein the oxazoline moiety and the thiazoline moiety are selected from the group consisting of formulas I–III:

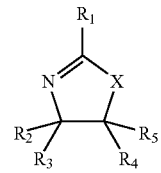

I

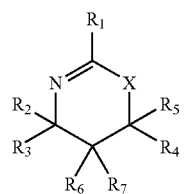

II

-continued

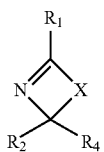

III wherein X is oxygen or sulfur; wherein $R_1$–$R_7$ are independently selected from the group consisting of hydrogen, a branched or linear $C_1$–$C_{20}$ alkyl group, a branched or linear $C_3$–$C_{20}$ cycloalkyl group, a branched or linear $C_6$–$C_{20}$ aryl group, a branched or linear $C_7$–$C_{20}$ alkylaryl group, and A.

3. The compound of claim 1, wherein Q is selected from the group of moieties consisting of a nitrone, a nitrile oxide and a nitrilimine.

4. The compound of claim 1, wherein Q is selected from the group consisting of formulas IV–VI:

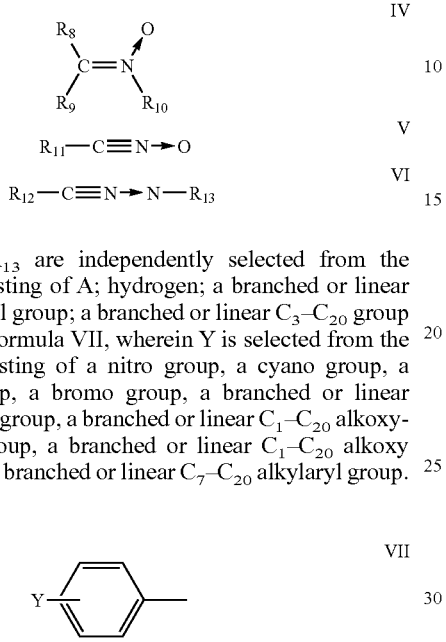

wherein $R_8$–$R_{13}$ are independently selected from the group consisting of A; hydrogen; a branched or linear $C_1$–$C_{20}$ alkyl group; a branched or linear $C_3$–$C_{20}$ group having the formula VII, wherein Y is selected from the group consisting of a nitro group, a cyano group, a chloro group, a bromo group, a branched or linear $C_1$–$C_{20}$ acyl group, a branched or linear $C_1$–$C_{20}$ alkoxycarbonyl group, a branched or linear $C_1$–$C_{20}$ alkoxy group, and a branched or linear $C_7$–$C_{20}$ alkylaryl group.

5. The compound of claim 1, wherein the allyltin moiety comprises the formula —CH=CHCH$_2$Sn($R_{14}$)$_3$, wherein $R_{14}$ is independently selected from the group consisting of a branched or linear $C_1$–$C_{20}$ alkyl group, a branched or linear $C_3$–$C_{20}$ cycloalkyl group, a branched or linear $C_6$–$C_{20}$ aryl group and a branched or linear $C_7$–$C_{20}$ alkylaryl group.

6. The compound of claim 1, wherein the alkoxysilane moiety comprises the formula —Si(OR$_{15}$)$_3$, wherein each $R_{15}$ independently contains one to about 6 carbon atoms.

7. The compound of claim 1, wherein A is selected from the group consisting of a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety.

8. The compound of claim 1, wherein A comprises [A'-(Z-A")$_k$], wherein A' and A" are independently selected from the group consisting of a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety; Z is oxygen, sulfur or C=O; and k is 1 to about 4.

9. The compound of claim 1, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiaz- olyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

10. A compound having the formula Q—A—B for promoting filler dispersion in a composition comprising a polymer containing unsaturated carbon-carbon bonds in its molecular structure and a filler having a surface group reactive with B, wherein:
   Q comprises a dipolar nitrogen-containing moiety that can form a 1,3 dipolar addition to an unsaturated carbon-carbon bond in the molecular structure of the polymer;
   B is selected from the group consisting of an oxazoline moiety, a thiazoline moiety, an alkoxysilane moiety and an allyltin moiety; and
   A is a linking atom or group that forms a bridge between Q and B.

11. The compound of claim 10, wherein the oxazoline moiety and the thiazoline moiety are selected from the group consisting of formulas I–III:

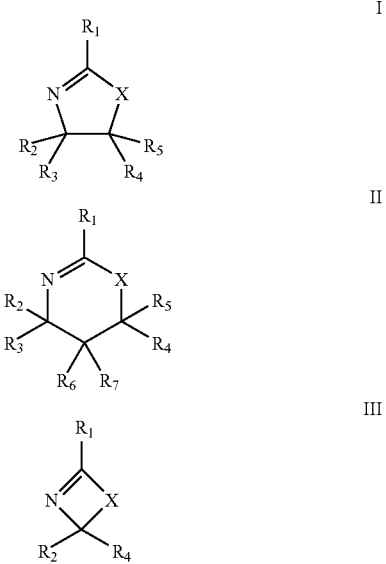

wherein X is oxygen or sulfur; $R_1$–$R_7$ are independently selected from the group consisting of hydrogen, a branched or linear $C_1$–$C_{20}$ alkyl moiety, a $C_3$–$C_{20}$ cycloalkyl moiety, a $C_6$–$C_{20}$ aryl moiety, a $C_7$–$C_{20}$ alkylaryl moiety, and A.

12. The compound of claim 10, wherein Q is selected from the group of moieties consisting of a nitrone, a nitrile oxide and a nitrilimine.

13. The compound of claim 10, wherein the allyltin moiety comprises the formula —CH=CHCH$_2$Sn($R_{14}$)$_3$, wherein $R_{14}$ is independently selected from the group consisting of a branched or linear $C_1$–$C_{20}$ alkyl group, a branched or linear $C_3$–$C_{20}$ cycloalkyl group, a branched or linear $C_6$–$C_{20}$ aryl group, a branched or linear $C_7$–$C_{20}$ alkylaryl group.

14. The compound of claim 10, wherein the alkoxysilane moiety comprises the formula. —Si(OR$_{15}$)$_3$, wherein each $R_{15}$ independently contains one to about 6 carbon atoms.

15. The compound of claim 10, wherein A is selected from the group consisting of a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety.

16. The compound of claim 10, wherein A comprises [A'-(Z-A")$_n$], wherein A' and A" are independently selected from the group consisting of a branched or linear $C_1$–$C_{20}$ alkylenyl moiety, a branched or linear $C_3$–$C_{20}$ cycloalkylenyl moiety, a branched or linear $C_6$–$C_{20}$ arylenyl moiety, and a branched or linear $C_7$–$C_{20}$ alkylarylenyl moiety; Z is oxygen, sulfur or C=O; and n=1 to about 4.

17. The compound of claim 10, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

18. The compound of claim 10, wherein the filler is selected from the group consisting of carbon black, silica, a mineral filler, and mixtures thereof.

19. The compound of claim 18, wherein the mineral filler is selected from the group consisting of silicates, talc, kaolin, clay, metal oxides, aluminum hydrate, mica, and mixtures thereof.

20. A method for modifying a polymer containing unsaturated carbon-carbon bonds in its molecular structure, the method comprising contacting said polymer with about 0.1 to about 30 percent by weight of said polymer of a compound having the formula Q—A—B to form a modified polymer, wherein Q comprises a dipolar nitrogen-containing moiety that forms a 1,3 dipolar addition to an unsaturated carbon-carbon bond; B is selected from the group consisting of an oxazoline moiety, a thiazoline moiety, an alkoxysilane moiety and an allyltin moiety; and A is a linking atom or group that forms a bridge between Q and B.

21. The method of claim 20, wherein Q is selected from the group of moieties consisting of a nitrone, a nitrile oxide and a nitrilimine.

22. The method of claim 21, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

23. A modified polymer produced by a method comprising the step of contacting a polymer having unsaturated carbon-carbon bonds in its molecular structure with about 0.1 to about 30 percent by weight of said polymer of a compound having the formula Q—A—B to form a modified polymer, wherein Q comprises a dipolar nitrogen-containing moiety that forms a 1,3 dipolar addition to an unsaturated carbon-carbon bond; B is selected from the group consisting of an oxazoline moiety, a thiazoline moiety, an alkoxysilane moiety and an allyltin moiety; and A is a linking atom or group that forms a bridge between Q and B.

24. The modified polymer of claim 23, wherein Q is selected from the group of moieties consisting of a nitrone, a nitrile oxide and a nitrilimine.

25. The modified polymer of claim 23, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenylnitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

26. A method for promoting filler dispersion in a polymeric composition, comprising the steps of:
(a) modifying a polymer having unsaturated carbon-carbon bonds in its molecular structure by reacting the polymer with about 0.1 percent to about 30 percent by weight of said polymer of a compound having the formula Q—A—B to form a modified polymer, wherein Q comprises a dipolar nitrogen-containing moiety that forms a 1,3 dipolar addition to an unsaturated carbon-carbon bond in the molecular structure of the polymer; B is selected from the group of filler-binding moieties consisting of an oxazoline moiety, a thiazoline moiety, an alkoxysilane moiety and an allyltin moiety; and A is a linking atom or group that forms a bridge between Q and B; and
(b) reacting the modified polymer with a filler comprising a surface group that binds to the B moiety of the compound.

27. The method of claim 26, wherein Q is selected from the group of moieties consisting of a nitrone, a nitrile oxide and a nitrilimine.

28. The method of claim 26, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

29. The method of claim 26, wherein the filler is selected from the group consisting of carbon black, silica, a mineral filler, and mixtures thereof.

30. The method of claim 29, wherein the mineral filler is selected from the group consisting of silicates, talc, kaolin, clay, metal oxides, aluminum hydrate, mica, and mixtures thereof.

31. A method for promoting filler dispersion in a polymeric composition, comprising the step of mixing together (i) a polymer having unsaturated carbon-carbon bonds in its molecular structure, (ii) about 0.1 percent to about 30 percent by weight of said polymer of a compound having the formula Q—A—B, wherein Q comprises a dipolar nitrogen-containing moiety that forms a 1,3 dipolar addition to an unsaturated carbon-carbon bond in the molecular structure of the polymer; B is selected from the group of filler-binding moieties consisting of an oxazoline moiety, a thiazoline moiety, an alkoxysilane moiety and an allyltin moiety; and A is a linking atom or group that forms a bridge between Q and B; and (iii) a filler comprising a surface group that binds to the B moiety of the compound.

32. The method of claim 31, wherein Q is selected from the group of moieties consisting of a nitrone, a nitrile oxide and a nitrilimine.

33. The method of claim 31, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

34. The method of claim 31, wherein the filler is selected from the group consisting of carbon black, silica, a mineral filler, and mixtures thereof.

35. The method of claim 34, wherein the mineral filler is selected from the group consisting of silicates, talc, kaolin, clay, metal oxides, aluminum hydrate, mica, and mixtures thereof.

36. A vulcanizable rubber composition, comprising:
(a) an elastomer containing unsaturated carbon-carbon bonds in its molecular structure;
(b) a hysteresis-reducing amount of a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B;
(c) a filler comprising a surface group that binds to the B moiety of the compound; and
(d) a cure agent.

37. The composition of claim 36, wherein the hysteresis-reducing amount of the compound is about 0.1 percent to about 30 percent by weight of the elastomer.

38. The composition of claim 36, wherein the elastomer is selected from the group consisting of homopolymers of conjugated diene monomers, and copolymers and terpolymers of the conjugated diene monomers with monovinyl aromatic monomers and trienes.

39. The composition of claim 36, wherein the elastomer is selected from the group consisting of natural rubber, synthetic polyisoprene, polybutadiene, polystyrene, styrene-butadiene copolymers, isoprene-butadiene copolymers, isoprene-styrene copolymers, terpolymers of styrene-isoprene-butadiene, acrylonitrile-butadiene rubber, terpolymers of acrylonitrile, butadiene and styrene, and combinations thereof.

40. The composition of claim 36, wherein the filler is selected from the group consisting of carbon black, silica, a mineral filler, and mixtures thereof.

41. The composition of claim 40, wherein the mineral filler is selected from the group consisting of silicates, talc, kaolin, clay, metal oxides, aluminum hydrate, mica, and mixtures thereof.

42. The composition of claim 36, wherein the cure agent comprises sulfur.

43. The composition of claim 36, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

44. A vulcanizable rubber composition comprising:
(a) a modified elastomer that comprises the reaction product obtained by contacting an elastomer having unsaturated carbon-carbon bonds in its molecular structure with compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B;
(b) a filler comprising a surface group that binds to the B moiety of the compound; and
(c) a cure agent.

45. The composition of claim 44, wherein the elastomer is selected from the group consisting of homopolymers of conjugated diene monomers, and copolymers and terpolymers of the conjugated diene monomers with monovinyl aromatic monomers and trienes.

46. The composition of claim 44, wherein the elastomer is selected from the group consisting of natural rubber, synthetic polyisoprene, polybutadiene, polystyrene, styrene-butadiene copolymers, isoprene-butadiene copolymers, isoprene-styrene copolymers, terpolymers of styrene-isoprene-butadiene, acrylonitrile-butadiene rubber, terpolymers of acrylonitrile, butadiene and styrene, and combinations thereof.

47. The composition of claim 44, wherein Q is selected from the group of moieties consisting of a nitrone, a nitrile oxide and a nitrilimine.

48. The composition of claim 44, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone;

4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

49. The composition of claim 44, wherein the filler is selected from the group consisting of carbon black, silica, a mineral filler, and mixtures thereof.

50. The composition of claim 49, wherein the mineral filler is selected from the group consisting of silicates, talc, kaolin, clay, metal oxides, aluminum hydrate, mica, and mixtures thereof.

51. The composition of claim 44, wherein the cure agent comprises sulfur.

52. A vulcanizable elastomeric composition, comprising:
  (a) the reaction product of (i) an elastomer having unsaturated carbon-carbon bonds in its molecular structure, (ii) a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B; and (iii) a filler comprising a surface group that binds to the B moiety of the compound; and
  (b) a cure agent.

53. The composition of claim 52, wherein the elastomer is selected from the group consisting of homopolymers of conjugated diene monomers, and copolymers and terpolymers of the conjugated diene monomers with monovinyl aromatic monomers and trienes.

54. The composition of claim 52, wherein the elastomer is selected from the group consisting of natural rubber, synthetic polyisoprene, polybutadiene, polystyrene, styrene-butadiene copolymers, isoprene-butadiene copolymers, isoprene-styrene copolymers, terpolymers of styrene-isoprene-butadiene, acrylonitrile-butadiene rubber, terpolymers of acrylonitrile, butadiene and styrene, and combinations thereof.

55. The composition of claim 52, wherein Q is selected from the group of moieties consisting of a nitrone, a nitrile oxide and a nitrilimine.

56. The composition of claim 52, wherein the compound is selected from the group consisting of 4-(2-oxazolyl)-phenyl-N-methyl-nitrone; 4-(2-thiazolyl)-phenyl-N-methyl-nitrone; 4-(2-oxazolyl)-phenyl-N-phenyl-nitrone; 4-(2-thiazolyl)-phenyl-N-phenyl-nitrone; phenyl-N-4-(2-oxazolyl)-phenyl-nitrone; phenyl-N-4-(2-thiazolyl)-phenyl-nitrone; 4-tolyl-N-4-(2-oxazolyl)-phenyl-nitrone; 4-tolyl-N-4-(2-thiazolyl)-phenyl-nitrone; 4-methoxyphenyl-N-4-(2-oxazolyl)-phenyl-nitrone; 4-methoxyphenyl-N-4-(2-thiazolyl)-phenyl-nitrone; 4-(2-oxazolyl)-phenyl-nitrile oxide; 4-(2-thiazolyl)-phenyl-nitrile oxide; 4-(2-oxazolyl)-phenyl-N-methyl-nitrilimine; 4-(2-thiazolyl)-phenyl-N-methyl-nitrilimine; 4-(2-oxazolyl)-phenyl-N-phenyl-nitrilimine; 4-(2-thiazolyl)-phenyl-N-phenyl-nitrilimine; phenyl-N-4-(2-oxazolyl)-phenyl-nitrilimine; phenyl-N-4-(2-thiazolyl)-phenyl-nitrilimine; and mixtures thereof.

57. The composition of claim 52, wherein the filler is selected from the group consisting of carbon black, silica, a mineral filler, and mixtures thereof.

58. The composition of claim 57, wherein the mineral filler is selected from the group consisting of silicates, talc, kaolin, clay, metal oxides, aluminum hydrate, mica, and mixtures thereof.

59. The composition of claim 52, wherein the cure agent comprises sulfur.

60. A vulcanized elastomeric compound, comprising the vulcanizable composition of claim 36.

61. A vulcanized elastomeric compound, comprising the vulcanizable composition of claim 44.

62. A vulcanized elastomeric compound, comprising the vulcanizable composition of claim 52.

63. A tire comprising at least one component that comprises a vulcanized elastomeric composition that comprises (i) the reaction product of an elastomer having unsaturated carbon-carbon bonds in its molecular structure, a filler selected from the group consisting of carbon black, silica, and mixtures thereof, and a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B; and (ii) a cure agent.

64. The tire of claim 63, wherein the component is a tire tread.

65. A method for making a vulcanized elastomeric composition, comprising the steps of
  (a) mixing together (i) an elastomer containing unsaturated carbon-carbon bonds in its molecular structure; (ii) a filler selected from the group consisting of carbon black, silica, a mineral filler, and mixtures thereof; (iii) a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B; and (iv) a cure agent; and
  (b) curing the composition.

66. A method for making a vulcanized elastomeric composition, comprising the steps of:
  (a) mixing together (i) a modified elastomer prepared by reacting an elastomer having unsaturated carbon-carbon bonds in its molecular structure with about 0.1 percent to about 30 percent by weight of said polymer of a compound having the formula Q—A—B, wherein Q comprises a dipolar nitrogen-containing moiety that forms a 1,3 dipolar addition to an unsaturated carbon-carbon bond in the molecular structure of the polymer; B is selected from the group of filler-binding moieties consisting of an oxazoline moiety, a thiazoline moiety, an alkoxysilane moiety and an allyltin moiety; and A is a linking atom or group that forms a bridge between Q and B; (ii) a filler selected from the group consisting of carbon black, silica, a mineral filler, and mixtures thereof and (iii) a cure agent; and
  (b) curing the composition.

67. A method for reducing the hysteresis of a rubber compound, comprising the steps of (a) mixing together (i) an elastomer containing unsaturated carbon-carbon bonds in its molecular structure; (ii) a filler selected from the group consisting of carbon black, silica, a mineral filler, and mixtures thereof; (iii) a hysteresis-reducing amount of a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B; and (iv) a cure agent; and (b) curing the composition.

68. A rubber compound having reduced hysteresis properties, comprising:

(a) the reaction product of (i) an elastomer having unsaturated carbon-carbon bonds in its molecular structure, (ii) a hysteresis-reducing amount of a compound having the formula Q—A—B, wherein Q comprises a dipolar nitrogen-containing moiety that forms a 1,3 dipolar addition to an unsaturated carbon-carbon bond in the molecular structure of the elastomer; B is selected from the group of filler-binding moieties consisting of an oxazoline moiety, a thiazoline moiety, an alkoxysilane moiety and an allyltin moiety; and A is a linking atom or group that forms a bridge between Q and B; and (iii) a filler comprising a surface group bound to the B moiety of the compound; and (b) a cure agent.

* * * * *